(12) United States Patent
Wells et al.

(10) Patent No.: US 7,185,552 B2
(45) Date of Patent: Mar. 6, 2007

(54) MOVABLE SAMPLE HOLDER

(75) Inventors: Peter John Wells, Gloucestershire (GB); Duncan Searle, Gloucestershire (GB); David Roberts McMurtry, Gloucestershire (GB)

(73) Assignee: Renishaw PLC, Gloucestershire (GB)

( * ) Notice: Subject to any disclaimer, the term of this patent is extended or adjusted under 35 U.S.C. 154(b) by 0 days.

(21) Appl. No.: 10/497,011

(22) PCT Filed: Nov. 27, 2002

(86) PCT No.: PCT/GB02/05338

§ 371 (c)(1),
(2), (4) Date: May 27, 2004

(87) PCT Pub. No.: WO03/046412

PCT Pub. Date: Jun. 5, 2003

(65) Prior Publication Data

US 2005/0028617 A1    Feb. 10, 2005

(30) Foreign Application Priority Data

Nov. 27, 2001  (GB) ................. 0128364.7
Dec. 12, 2001  (GB) ................. 0129670.6
May 14, 2002  (GB) ................. 0210925.4

(51) Int. Cl.
  *G01N 37/00*  (2006.01)
  *A61C 19/10*  (2006.01)
  *B24B 49/04*  (2006.01)

(52) U.S. Cl. .................. 73/864.91; 73/865.8; 269/57; 433/49; 433/51

(58) Field of Classification Search ............. 73/864.91, 73/865.8; 269/55–58, 60–62, 71; 433/26, 433/49–52, 163, 171, 201.1, 202.1
See application file for complete search history.

(56) References Cited

U.S. PATENT DOCUMENTS 3,004,445 A * 10/1961 Mondon .................. 74/424.92
3,456,548 A *  7/1969 Schaub et al. ............. 411/403
4,234,152 A * 11/1980 Browse ..................... 248/415
4,375,770 A *  3/1983 Druet ...................... 74/424.92
5,247,846 A    9/1993 Grossmann et al.
6,095,476 A *  8/2000 Mathis ...................... 248/422
6,106,365 A *  8/2000 Gessler ......................... 451/8

FOREIGN PATENT DOCUMENTS

EP   0 455 855 A1   11/1991
EP   0 634 150 B1    2/1999

* cited by examiner

*Primary Examiner*—Hezron Williams
*Assistant Examiner*—David A. Rogers
(74) *Attorney, Agent, or Firm*—Oliff & Berridge, PLC (57) ABSTRACT

A device for the axial and rotational movement of a sample is disclosed comprising a mount member for mounting the sample, which is rotatable about and movable along an axis, characterised in that the mount member has a helical screw thread which produces the movement along said axis simultaneously with the rotation. A sample may be scanned or machined whilst being axially and rotationally moved. The screw thread may be disengageable perphaps by relative movement of co-operating screw threads into and out of engagement with each other by a lever to allow movement of the mount member along the axis without rotation when desired. The screw thread on one of the members may be formed from a piece or layer of a deformable material, which deforms to form a mating screw thread upon being brought into engagement with the screw thread on the other member. Also desclosed is a method of scanning a sample.

12 Claims, 9 Drawing Sheets

CONFIRMATION COPY

MOVABLE SAMPLE HOLDER

This invention relates to a device allowing axial and rotational movement of a sample holder.

In certain circumstances, it is desirable to be able to move a sample holder, for example, when scanning the form of a 3-dimensional object in order to be able to reproduce the form. One such circumstance is in the reproduction of teeth or dental parts, e.g. when bridge work etc. is required. An accurate 3-dimensional picture of the tooth or other dental part is required in order to manufacture a replacement. Therefore, the scan must cover a substantial proportion of the surface area of the tooth. It is also desirable, from both time and accuracy aspects, that the dental part be completely scanned in one process.

One device which enables the scanning of a dental part in one process is described in EP 0 634 150. The device comprises a rotatable holder onto which the dental part is placed. The vertical movement is provided by having a reciprocally displaceable scanning device. A problem with this device is that it is complicated requiring two separate motions thus, two motors which have to be co-ordinated. The use of two motors also increases the cost and the chances of device failure.

The present invention provides a device for the axial and rotational movement of a sample, comprising a mount member for mounting the sample, the mount member being rotatable about an axis and movable along said axis, characterised in that the mount member has a generally helical screw thread which produces the movement along said axis simultaneously with the rotation.

We have found it desirable that the axial movement per rotation of the mount member and sample holder is small enough that a substantial proportion of the surface of the dental part or tooth is scanned. This requires the use of a thread with a fine pitch, allowing for very small increments along the axis for each revolution of the sample holder. However, we also find it desirable to provide for rapid movements along the axis, without the multiple rotations required by a fine thread. This enables, for example, convenient adjustment of sample position when small increments are not required.

Therefore, the screw thread is preferably disengageable to allow movement of the mount member along the axis without rotation when desired.

More particularly, the screw thread on the mount member may co-operate with a screw thread on a relatively fixed member, and the screw threads may be relatively movable into and out of engagement with each other. We have found it particularly advantageous if the screw thread on one of the members is formed from one or more pieces or a layer of a deformable material, which deforms to form a mating screw thread upon being brought into engagement with the screw thread on the other member.

Alternatively both the screw threads of the mount member and relatively fixed member are permanently formed i.e. are turned or otherwise formed in the respective surfaces of the two members.

Preferably, the device further comprises a probe or machine tool wherein a sample is scanned or machined whilst being axially and rotationally moved.

In a preferred embodiment the probe or machine tool is capable of being positioned relative to the rotational axis of the mount member.

Preferably the sample is a dental part.

Preferably, the relative movement of the screw threads into and out of engagement with each other is actuated by a lever. The lever is movable between two positions, one position of the lever corresponding to engagement of the screw threads, the other position corresponding to non engagement of the screw threads.

In a preferred embodiment, the device further comprises a plurality of pieces of hard material radially spaced around the relatively fixed member. These hard pieces form a slide for one of the screw threads when the mating screw threads are not engaged.

According to a second aspect of the invention there is provided a method of a scanning a sample comprising the steps of:
 providing a mount member having a sample mounted on one end the mount member being rotatable about an axis and movable along said axis wherein the mount member has a generally helical screw thread which produces movement along said axis simultaneously with the rotation;
 positioning a probe at a suitable point on the surface of the sample; and
 rotating the mount member characterised in that the mount member rotates in a generally helical path producing a spiral scan of the surface of the sample.

Preferably the sample is a dental part.

Alternatively, the sample could be machined by a machine tool instead of scanned by a probe.

The invention will now be described by example and with reference to the accompanying drawings, of which.

Figure 1:
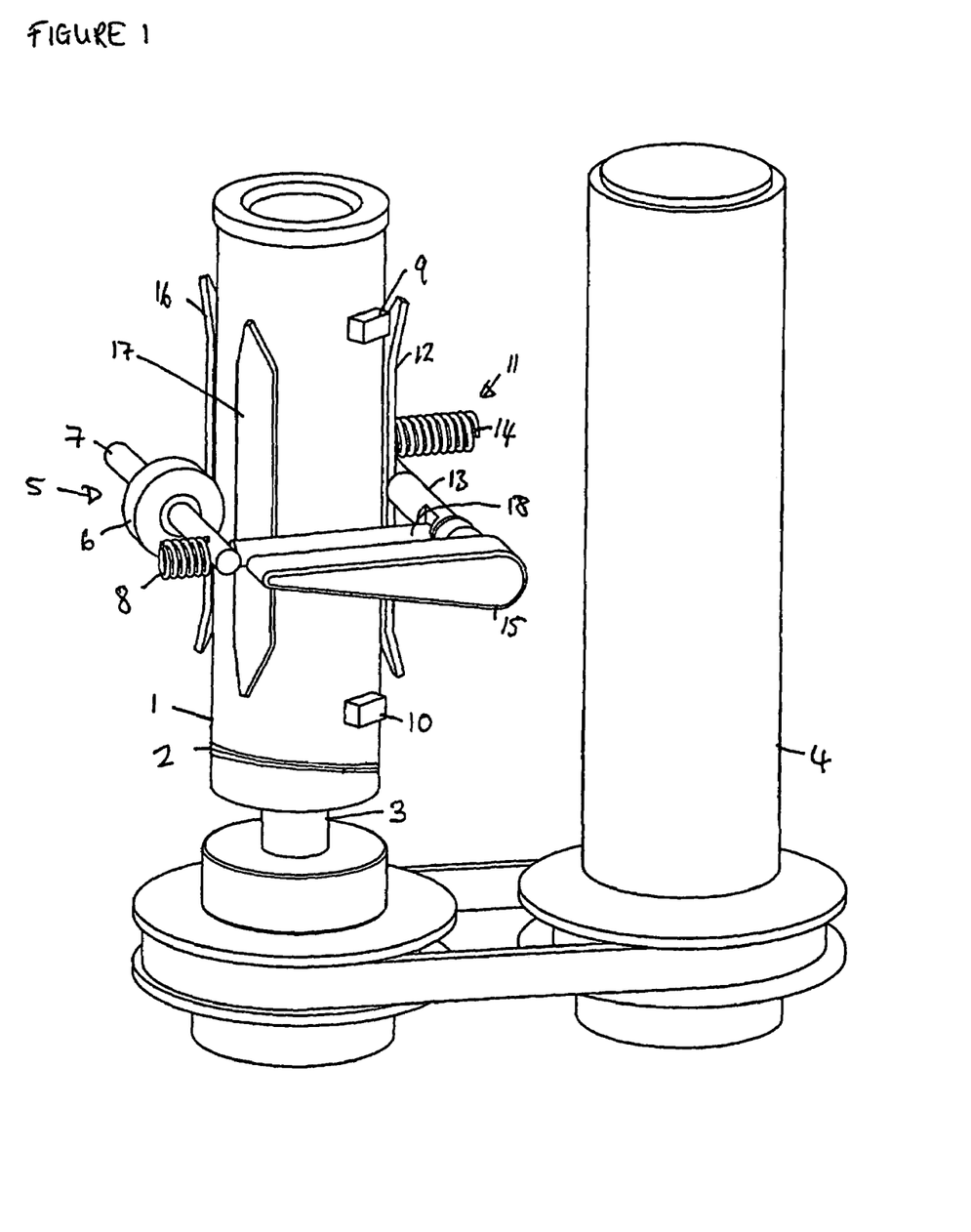
FIG. 1 shows an exploded view of a device according to the invention.

FIG. 1 shows a device according to the invention having a mount member 1 with a helical screw thread 2 running around the outside circumference. The mount member 1 is mounted on a drive spindle 3 which is driven by a motor 4. A first biasing means 5, is a PTFE roller 6 mounted on a first shaft 7 which is substantially perpendicular to the mount member 1 and is biased by a first spring 8 towards the mount member 1. Two pads of PTFE 9, 10 are placed in spaced relationship along the length of the mount member 1 each located about 120° from the PTFE roller 6. Two further such PTFE pads (not shown) are similarly spaced and located at about 120° to both the roller 6 and the pads 9,10.

A second biasing means 11, is a first piece of hard material 12 retained by a second shaft 13 which is substantially perpendicular to the mount member 1, the second shaft having a second spring 14 at one end and a lever 15 at the other end. The first piece of hard material 12 is positioned adjacent the mount member 1 diametrically opposite the PTFE roller 6. The second biasing means 11 is of equal or greater and opposite force to the first biasing means 5. Two further pieces of hard material 16, 17 are spaced circumferentially with respect to the first piece of hard material 12 and each other around the mount member 1. The second shaft 13 is in mechanical communication with the first shaft 7 via a rod 18. The lever 15 is movable between a first position in which the second biasing means 11 is not actuated and a second position in which the second biasing means 11 is actuated.

For clarity, a relatively fixed member which houses the mount member 1 within a hollow circular shaft has been omitted from this figure. The shaft is provided with a number of recesses which house the components of the first and second biasing means as well as the four pads of PTFE and the two further pieces of hard material. The screw thread 2 has a pitch of 0.2 mm and is manufactured on the surface of the mounting member 1 via a turning process. The mounting member 1 has a diameter of 20 mm. When a screw thread is less than 0.3 millimetres it is extremely difficult to manufacture the mate (either the female or male thread). This is particularly true when a constant and smooth movement between the screw threads is required i.e. when a good match between the threads is required. Thus, a deformable material, such as PTFE, is provided to produce the mating thread. This overcomes the potential problems associated with having two machined threads.

In order to produce the mating thread, four pads of PTFE 9,10 (and not shown) are provided at different locations along and around the screw thread 2. The location of pads of PTFE is maintained by partially housing them in recesses provided in the shaft of the relatively fixed member (not shown) in which the mount member is housed. When the pads of PTFE are in contact with the screw thread 2, they deform and take the shape of a mating thread. This enables the mounting member to move relative to the pads of PTFE 9,10 (and thus the relatively fixed member) in a helical path when the mount member is rotated by the motor 4.

Regardless of the position of the lever 15, the first biasing means 5 is always actuated. However, when the lever 15 is in its second position, the second biasing means 11 is also actuated. As the second biasing means 11 opposes and at least equals the force of the first biasing means 5 this results in the effect of the first biasing means being cancelled by the second biasing means.

When the lever 15 is in its first position, the pads of PTFE are in contact with the screw thread 2 hence, they deform and the mating thread is produced in the pads of PTFE 9, 10. Thus, in this first position, the vertical movement of the mount member is controlled by the rate of rotation of the mount member. The rotation of the mount member is controlled by motor 4 which preferably has variable rpm.

In order to enable a fast repositioning of the height of the mount member 1 when small increments are not required, the pads of PTFE 9, 10 need to be disengaged from the screw thread 2 of the mount member 1. This is achieved by actuating the lever 15 into the second position. When the lever 15 is actuated into the second position, the rod 18 pushes against the first shaft 7 canceling out the biasing effect of the first spring 8 thus removing the bias from the PTFE roller 6. Simultaneously, the first piece of hard material 12 is biased towards the mount member 1. This moves the mount member 1 towards the further pieces of hard material 16,17 and out of engagement with the mating thread in the pads of PTFE 9, 10. The three pieces of hard material 12,16,17 form a slide on which the mount member may be moved up and down independently of any rotation of the mount member. Thus, in order to position a tooth or other sample in approximately the right position for scanning, the lever would be placed in its second position, which allows rapid movement up or down, once at approximately the right height, the lever is moved into its first position enabling fine adjustments to the height to be made prior to scanning.

The device could be used without the pieces of hard material however, as the PTFE deforms into the screw threads, there is a chance that the PTFE will still co-operate or engage with the screw threads after the second biasing means has been actuated by movement of the lever to its second position and thus may be eroded by large scale movement of the screw thread (that which is independent of the rotation of the screw thread). This would result in a limitation of the lifetime of the device or necessitate replacement of the pads of PTFE from time to time.

The deformable material does not have to completely fill the screw thread, in fact this would be undesirable as it would make it difficult for the deformable material to disengage from the screw threads on movement of the mount member to its second position. The deformable material merely has to co-operate sufficiently with the screw thread in order that the mount member does not slip when it is rotated. Therefore the formation of a shallow mating screw thread is preferred.

Figure 2A:
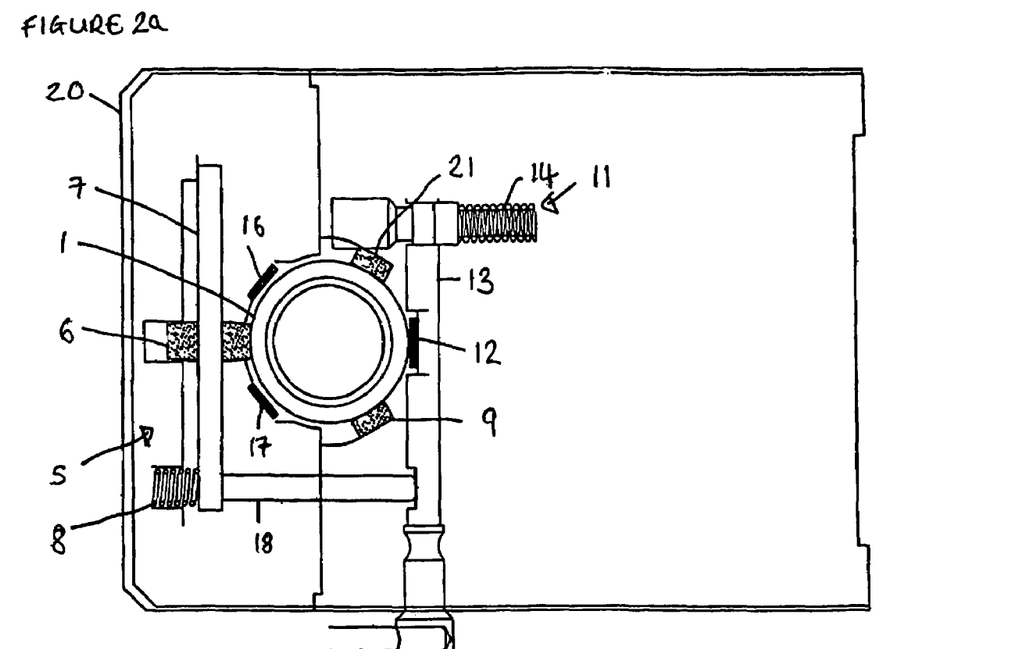
FIGS. 2a and 2b show plan views of the device shown in FIG. 1.
Figure 2B:
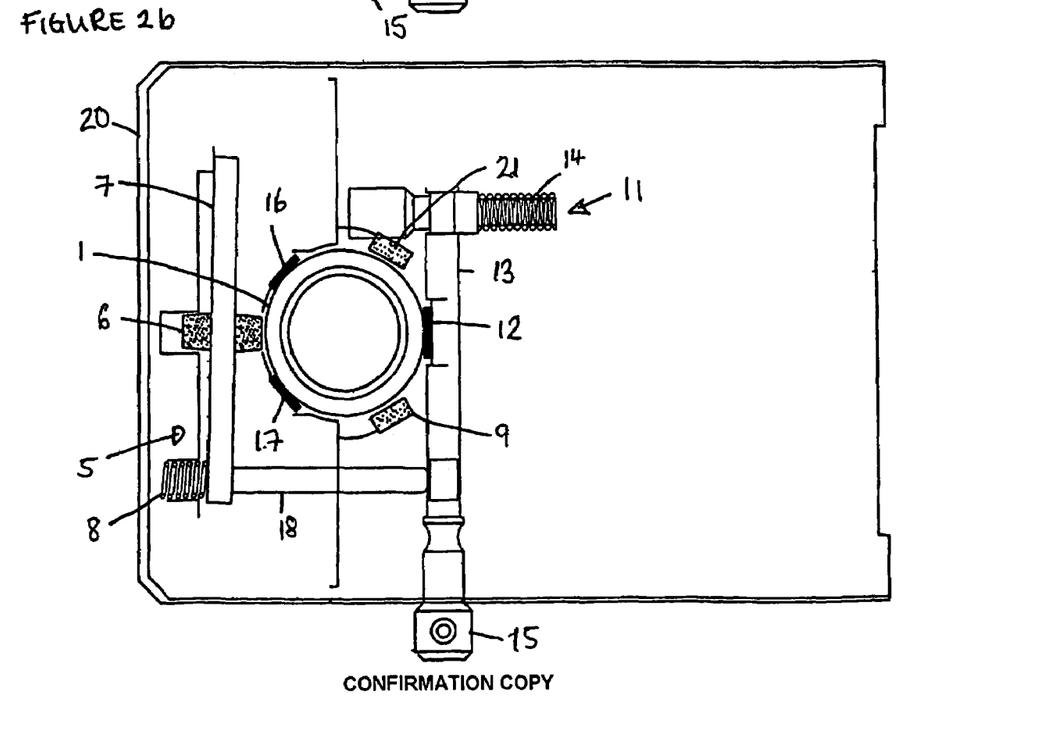

FIGS. 2*a* and 2*b* show plan views of the device shown in FIG. 1. A mount member 1 with a helical screw thread (not shown) on its outer circumference is housed within a relatively fixed member 20. A first biasing means 5 comprises a first spring 8, a first shaft 7 and a PTFE roller 6 mounted on the first shaft 7. Two pads of PTFE 9,21 are housed between the screw thread on the mount member and the relatively fixed member approximately 120° from the PTFE roller 6 (further pads of PTFE may be placed along the length of the relatively fixed member). A second biasing means 11 which is located adjacent the mount member and diametrically opposite the first biasing means 5, comprises a second shaft 13 to which is attached at one end a second spring 14 and at the other end a lever 15 which is moveable between two positions. The second shaft 13 is in mechanical communication with the first shaft 7 via a rod 18. The second shaft 13 has a first piece of phosphor bronze 12 attached thereto. This first piece of phosphor bronze 12 is located diametrically opposite the PTFE roller 6. Two further pieces of phosphor bronze 16,17 are located about 120° away from the first piece of phosphor bronze in the wall of the relatively fixed member.

In FIG. 2*a*, the lever 15 is in the first position. In this first position, only the first biasing means 5 is actuated. The PTFE roller 6 is biased by the first spring 8 into mechanical communication with the mount member 1. This causes the screw thread of the mount member 1 to engage with the two pads of PTFE 9,21 forming a mating screw thread in the PTFE. This first position produces rotation of the mounted member with respect to the relatively fixed member simultaneously with a vertical displacement i.e. the mount member moves with a helical motion.

In order to disengage the two screw threads, the lever 15 is actuated into its second position. When the lever is in the second position, the second biasing means 11 is actuated and opposes the first biasing means 5. The movement of the lever 15 to the second position causes a number of things to occur. Firstly, the rod 18 which mechanically joins the first and second shafts, is pushed towards the first shaft and against the first biasing means neutralising it. In order to negate the first bias, this force, which acts in the opposite direction to the first bias, must be at least equal the force of the first bias. Secondly, and simultaneously, the first piece of phosphor bronze 12 is pushed into contact with the mount member 1. Due to the relative positions of the two pads of PTFE and the first piece of phosphor bronze, this acts to disengage the screw thread of the mount member 1 from the screw thread formed in the two pads of PTFE 9,21.

The hard material has a substantially smooth, flat surface which will not deform to the shape and configuration of the screw thread thus, the screw thread is able to slide up and down the surface of the hard material regardless and independent of rotation of the mount member. The hard material may be spring steel or phosphor bronze for example.

The PTFE roller 6 need not be made from PTFE or indeed any deformable material and need not be a roller. The PTFE roller 6 biases the mount member 1 towards the pads of PTFE 9,10,21 in order that the screw thread on the mount member co-operates and engages with the pads of PTFE thus and producing a mating thread in the pads of PTFE. An alternative to a PTFE roller is a pad of hard material.

The relatively fixed member has an inner diameter approximately 0.5 mm larger than the outer diameter of the screw thread in order to enable the screw threads of the mount member to move into and out of engagement with the mating screw thread.

When a scan of an object is to be performed, the position of the object relative to the scanning device is important. Additionally, the scanning device will have a window of x,y,z co-ordinates in which it is most accurate so it is important for the whole scan to be conducted within this window. Further, the scanning device will have a limited range of movement of, for example, the probe (perhaps an LVDT) which actually conducts the scan so, in order to ensure a good scan, the whole object must be within this range of movement.

In order to ensure repeatable repositioning of the mount member and thus a tooth with respect to a relatively fixed member and thus a scanning device, the mount member is preferably kinematically held in the first position. "Mechanical Design of Laboratory Apparatus" by H Braddick, Chapman and Hall Ltd, London 1960 details the principles of kinematic location.

For axial movement with kinematic location of the mount member within a relatively fixed member, five points of contact are required. There are a number of configurations of the pieces that can be used, one of the most stable being to form two triangular shapes from the five pieces although other forms may be used, with the apex of each triangle being the PTFE roller. When a triangular configuration is used, the PTFE roller should be placed substantially diametrically opposite the mid-point between the other pieces of deformable material on the circumference of the mount member.

Although five points of contact are required for the kinematic location of the mount member within the relatively fixed member, this does not mean that each pad of PTFE can only comprise one point of contact. As an alternative, three pieces of PTFE may be used, the PTFE roller maintaining one continuous point of contact with the screw thread but, the other two pads of PTFE each having two points of contact with the screw thread, making five points of contact in total. This can be achieved by having rectangular shapes or o-rings of the deformable material, although other shapes will be apparent to the person skilled in the art. Rectangular pieces and o-rings are placed with their longitudinal axis placed radially with respect to the mount member. In order to obtain two points of contact instead of one continuous point of contact, the central portion of each rectangle or a selected portion of each o-ring does not co-operate with the screw thread when deformed. One way to achieve the two points of contact from one pad of PTFE is by design of the recess in the relatively fixed member in which the pad is housed. If the recess is provided with two flat portions then the PTFE will protrude further from the recess at these flat portions than where there is no flat portion. This results in the PTFE interacting with the screw thread on the mount member prior to parts of the PTFE which are not housed in these flat zones. In order to ensure that just these two portions corresponding to the flat portions of the housing engage with the screw thread on the mount member, the force of the first biasing means must be carefully set.

Figure 3:
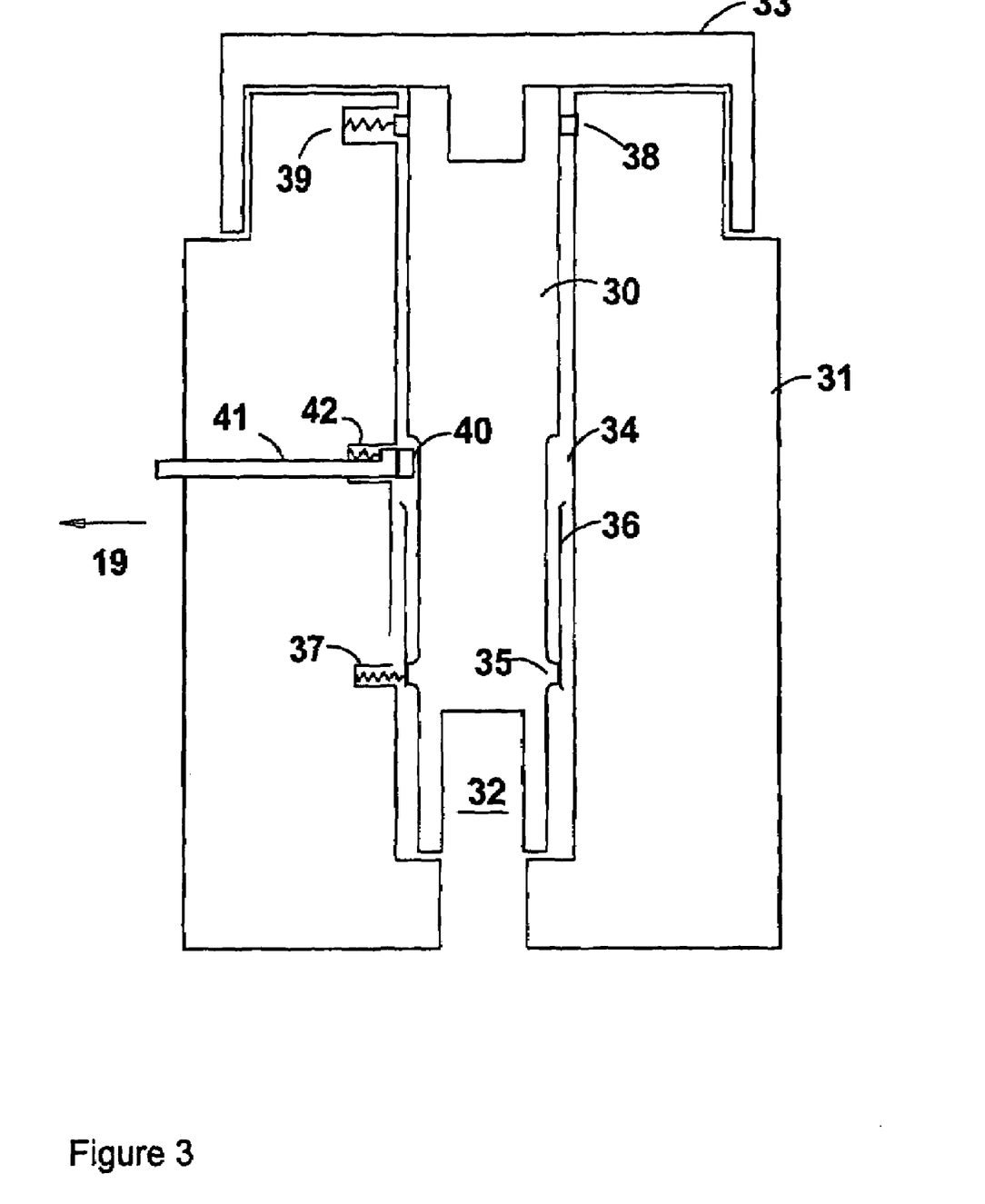
FIG. 3 shows a cross-section of a device according to the invention.

FIG. 3 shows a cross-section of a device according to the invention having a mount member 30 housed within a relatively fixed member 31. The mount member 30 is mountable at one end on a drive spindle at 32 which is driven by a motor (not shown), the other end of the mount member 30 is attached to a turntable 33 onto which a sample holder may be secured. The mount member 30 has a relieved portion 34 along its length which extends towards the drive spindle end 32 from near the longitudinal mid-point of the mount member 30. This relieved portion 34 has a screw thread (not shown) formed thereon, and is of sufficiently less diameter than the unrelieved portion to accommodate the screw thread therein. At the end of the relieved portion 34 which is proximate the drive spindle end, there is a collar 35 which has a diameter which at least equals that of the unrelieved portion of the mount member 30. Radially spaced 120° apart around the mount member 30, in the vicinity of the collar 35 are three pieces of hard material 36. A first spring 37 biases one of the pieces of hard material 36 towards the other two which are fixed to the housing 31.

At the distal end of the mount member 30, is a further set of three supports 38 which are radially spaced 120° apart and aligned with the pieces of hard material 36. A second spring 39 is vertically in line with the first spring 37 and thus biases one of the further set of supports 38 in the same direction as the first spring i.e. towards the other two which are fixed to the housing. Thus, the position of the mount member 30 within the housing 31 is maintained by the action of the two springs 37,39.

The pieces of hard material and further set of supports support the mount member 30 and form a slide when the screw thread (not shown) on the mount member 30 is disengaged from its mating thread.

The mating thread (not shown) for the screw thread machined onto mount member 30 is formed in a piece of soft material 40 which is attached to a handle 41. The handle 41 is secured to the relatively fixed member 31 in a location that corresponds to the relieved portion 34 of the mount member by a third spring 42. The third spring 42 biases the handle 41 such that the rest position of the handle is with the soft material in engagement with the thread on the mount member 30. By pulling 19 the handle 41 away from the mount member 30, the bias provided by spring 42 is overcome and the soft material 40 is removed from the engaged position into a second position where the soft material 40 is no longer engaged with the screw thread on the mount member.

When the soft material 40, such as PTFE, is engaged with the screw thread on the mount member 30, vertical movement of the mount member and turntable 33 is a function of the speed of rotation of the drive spindle and the pitch of the screw thread.

When the soft material 40 is not engaged with the screw thread, the mount member 40 slides up and down the pieces of hard material 35 and the further supports 38.

Figure 4:
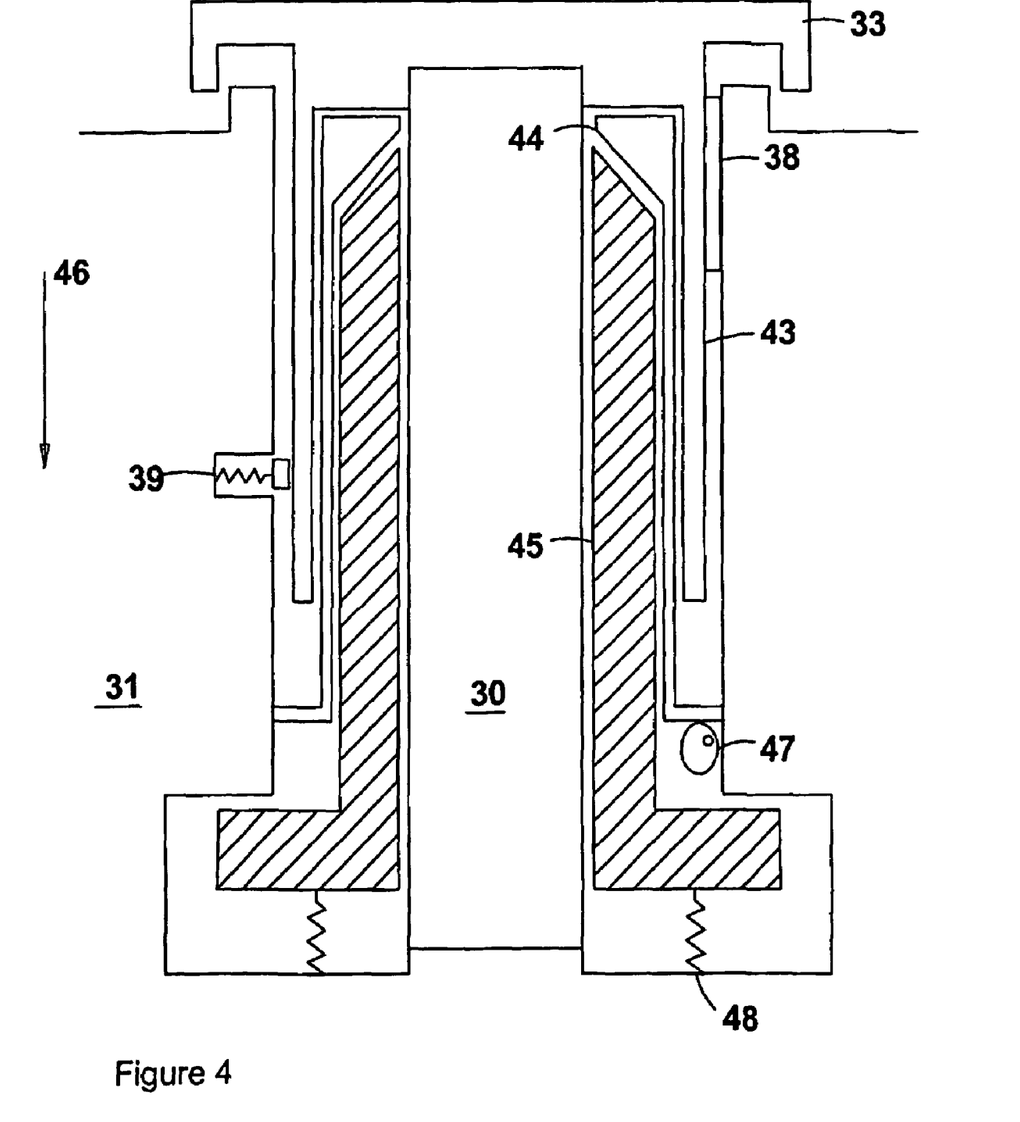
FIG. 4 shows a cross-section of a further embodiment of the invention.

FIG. 4 shows a cross-section through a further embodiment of the invention. A mount member 30 is housed within a relatively fixed member 31 and is mounted at one end on a drive spindle (not shown). At the distal end of the mount member 30 a turntable 33 (onto which a sample holder may be secured) is attached. A screw thread (not shown) is formed on the circumference of the mount member 30. The turntable 33 has a downwardly extending sleeve 43 which lies between the relatively fixed member 31 and the mount member 30. A set of three supports 38 are radially spaced 120° apart and longitudinally displaced with respect to each other, positioned between the sleeve 43 and the relatively fixed member 31. A spring 39 biases one of the supports towards the other two which are fixed to the relatively fixed member 31. These supports maintain the centre of rotation of the turntable 33 on the rotary axis of the mount member 30.

Between the sleeve 43 and the mount member is an insert 44 and a piece of deformable material 45. The insert 44 is attached to the relatively fixed member 31 and movable between an engaged and non-engaged (as shown) positions by a cam 47. The piece of deformable material 45 is fixed to the relatively fixed member 31 at one end by three springs 48 and extends longitudinally along and radially around the mount member 30 towards the turntable 33. Thus, the deformable material 45 is positioned between the insert 44 and the mount member 30. The deformable material 45 has an inclined surface which co-operates with the insert 44 and will deform to form a mating thread to the screw thread on the mount member 30 when in contact with the screw thread.

As shown, in the diagram, the screw thread on the mount member 30 is not engaged with a mating thread and so the turntable is freely movable in the plane of the rotary axis out of the relatively fixed member 31.

If however, the cam 47 is actuated by, for example, moving a lever, the insert 44 moves downwards 46 and engages the inclined surface of the deformable material 45 and forces it towards the mount member 30 where it deforms and forms a mating thread.

If the actuation of the cam 47 is reversed by, for example, returning a lever to its previous position, the downwards force on the insert 44 is removed and the insert 44 no longer forces the deformable material 45 into engagement with the screw thread.

In this embodiment, the deformable material is nylon which has, either by virtue of its method of manufacture and/or a subsequently machining process, a natural bias which causes it to lean away from the mount member 30 thus ensuring that the deformable material 45 does not accidentally engage the screw thread on the mount member 30. The insert 44 is made from a material such as brass or steel which is harder than the deformable material.

Figure 5:
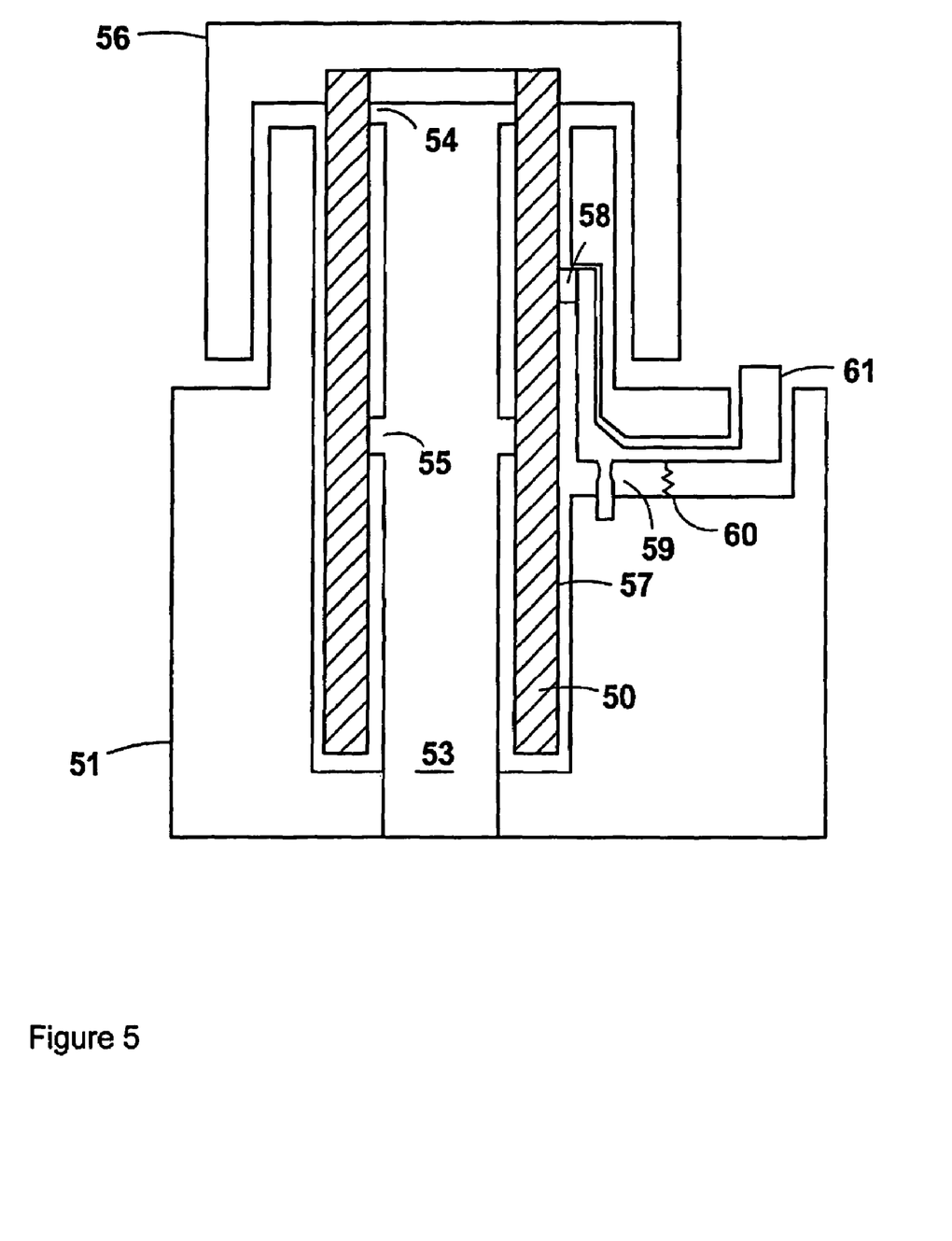
FIG. 5 shows a cross-section of an alternative device according to the invention.

FIG. 5 shows a cross-section through an alternate. device having a hollow mount member 50. The relatively fixed member comprises a housing 51 and a pillar 53. The pillar 53 is fixed to the housing 51 and extends within the hollow centre of the mount member 50 i.e. the mount member is located between the housing and pillar. The pillar has two sets of contact points 54,55 each of which consist of two areas of greater radius than the rest of the pillar 53 and which are longitudinally displaced along the length of the pillar from each other and are radially disposed 120° apart from each other and a third contact point (not shown) which lies longitudinally between contact points 54 and 55 and which is biased into contact with the pillar. 53 by a spring and thus maintains the relative positions of the pillars 53 and mount member 50 in the radial direction. The contact points 54,55 thus also maintain the position of the mount member 50 with respect to the housing 51. The mount member 50 has a turntable 56 attached to one end onto which a sample or sample holder may be placed.

A screw thread 57 is located on the external circumference of the mount member 50. A mating thread for the screw thread 57 is formed in a piece of deformable material 58. The deformable material 58 which is PTFE, is attached to a flexure hinge 59 formed from a plastic material such as nylon. A spring 60 biases the hinge so that the normal operating position for the deformable material 58 is in contact with the screw thread 57. Actuation of a lever 61 opposes the biasing force of the spring 60 and moves the deformable material 58 away from the screw thread 57.

When the mount member 50 is driven by a motor (not shown) and the deformable material 58 is in its normal operating position (in contact with the screw thread) the mount member 50 and the turntable 56 rotate with respect to the housing 51 and pillar 53. Actuation of the lever 61 moves the deformable material 58 away from the screw thread 57 so the screw thread 57 is no longer engaged with a mating thread. The mount member 50 and turntable 56 may now be moved vertically relative to the housing 51 and pillar 53 independently of rotational movement of the mount member 50.

Figure 6:
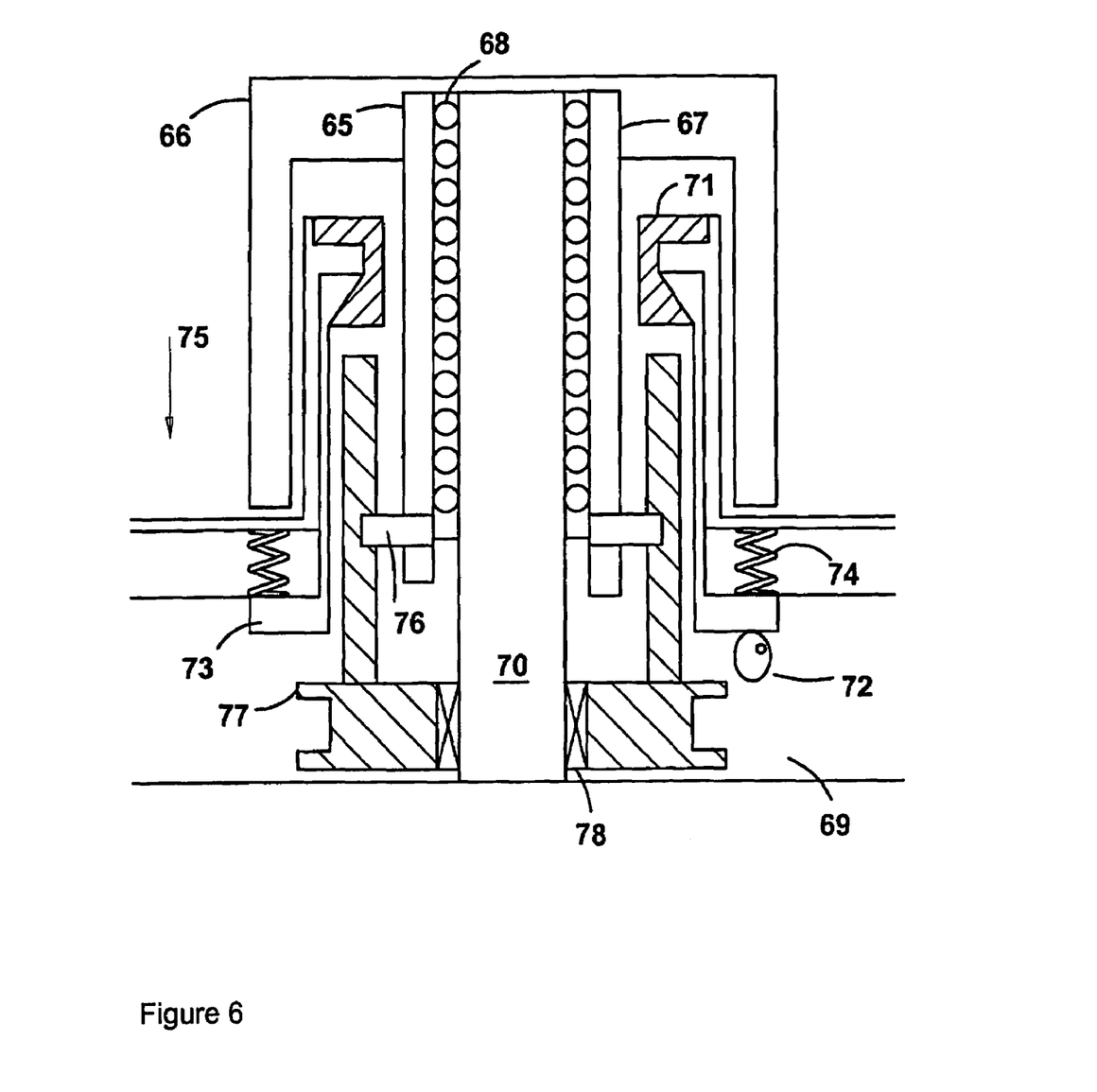
FIG. 6 shows a cross-section of a device according to the invention.

FIG. 6 shows a cross-section of a device having a mount member 65 attached to a turntable 66. The mount member has a screw thread 67 on its outer circumference and an internal linear rotary bearing 68 mounted on an internal shaft 70. The internal shaft 70 is fixed to the housing 69. This linear rotary bearing 68 enables the mount member 65 and the turntable 66 to be rotated with respect to a housing 69 and the internal shaft 70. The mount member 65 has, near the distal end to that attached to the turntable 66, a number of spurs 76 which project radially from the mount member. The spurs 76 engage with a corresponding number of slots which are radially disposed in a circular drive pulley 77 which is mounted via bearings 78 on the internal shaft 70. The circular drive pulley 77, when attached to a motor (not shown) rotates which, as the spurs 76 is are engaged to the drive pulley 77 causes rotation of the mount member 65 and turntable 66 on the linear rotary bearing 68.

A wedge shaped ring of deformable material 71 is fixed within the housing 69. This ring of deformable material 71 is actuated between two positions by an ellipsoidal cam 72 which acts on one end of a tube-like actuator 73 via three radially disposed springs 74. The distal end of the tube-like actuator 73 rests against the inclined face of the wedge of deformable material 71.

When the cam 72 has its major axis acting on the actuator 73 and springs 74 (as shown in the figure), the springs 74 are compressed and the actuator 73 rests against the deformable material 71 without significantly distorting the deformable material 71. this means that the deformable material 71 does not contact the screw thread 67.

When the cam 72 is rotated through 90°, thus having its minor axis acting on the actuator 73 and springs 74, the springs relax from their original compressed state and the actuator 73 is moved in the direction of arrow 75. This causes movement of the deformable material 71 towards and into contact with the screw thread 67 where it forms a mating thread which enables helical movement of the turntable 66 on rotation of the mount member 67 by the circular drive pulley 77.

Figure 7:
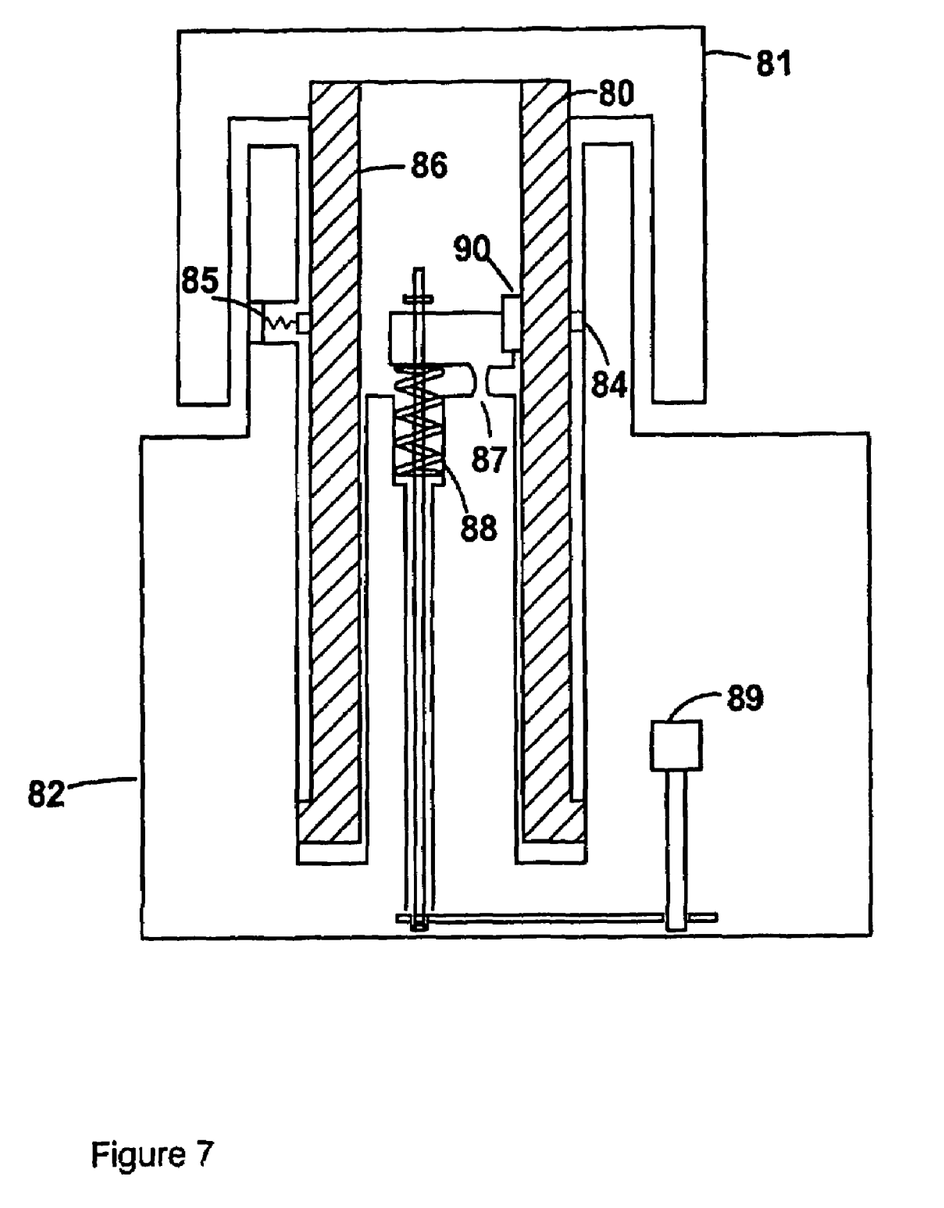
FIG. 7 shows a cross-section of a further device according to the invention.

FIG. 7 shows a cross-section of a further device having a hollow mount member 80 which is attached to a turntable 81. The hollow mount member 80 is housed within a relatively fixed member.

Between the hollow mount member 80 and the relatively fixed member 82 is a set of three radial disposed supports 84 spaced 120° apart from each other around the external circumference of the hollow mount member 80. A spring 85 biases one of the supports 84 towards the other two which are secured to the relative fixed member.

On the internal circumference of the hollow mount member 80 is a screw thread 86. Within the hollow of the mount member 80 and secured to the relatively fixed member 82 is a flexure hinge 87 made from a piece of plastic such as nylon. The flexure hinge 87 is biased into a contact position by a second spring 88. A lever arrangement 89 enables actuation of the flexure hinge 87 into a second non-contact position. When the flexure hinge 87 is in the contact position (as shown in the figures), a piece of PTFE 90, which is secured to one side of the flexure hinge 87, contacts the screw thread 86. In this contact position, rotation of the hollow mount member 80 with respect to the relatively fixed member 82 and flexure hinge 87 causes vertical movement of the hollow mount member 80 and turntable 81 at a rate determined by the speed of rotation and the pitch of the screw thread 86.

When the lever 89 is actuated, moving the flexure hinge 87 into is second non-contact position (not shown), the PTFE 90 is moved radically inwards and away from the screw thread 85 thus it no longer provides a mating thread which abuts the screw thread 86 and enables the hollow mount member to describe a helical path.

The supports 84 tend to maintain the position of the hollow mount member 80 with respect to the rotational axis of the device regardless of whether the flexure hinge 87 is in its contact or non-contact position. This means that samples may be secured to the centre of the turntable 81 with confidence that they are at the centre of rotation.

Figure 8:
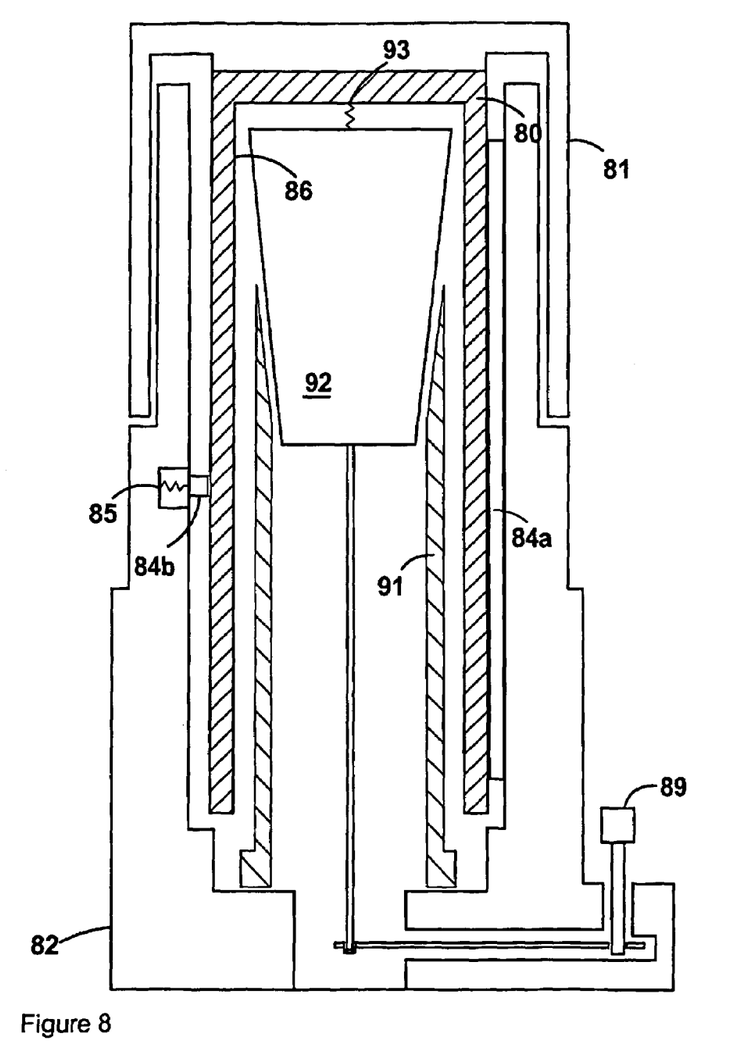
FIG. 8 shows a cross-section of a further embodiment of the invention.

FIG. 8 shows a cross-section of a further embodiment of the invention having a hollow mount member 80 with a screw thread 86 on its internal surface. The hollow mount member 80 is housed within a relatively fixed member 82. Three supports 84a,84b are radially disposed around the mount member spaced 120° apart from each other. The supports 84a extend substantially along the length of the mount member 80 whereas support 84b is located approximately centrally along the length of the mount member 80. A spring 85 biases one of the supports 84b towards the other two 84a which are secured to the relatively fixed member 82. A sleeve of deformable material 91, for example nylon, is housed within the hollow mount member 80. This sleeve 91 is designed and/or manufactured with a natural bias that inclines away from the screw thread 86 i.e. radially inwards. Partially journalled within the sleeve 91 is a bung 92. The bung 92 is connected to the inside upper surface of the hollow mount member 80 via a spring 93. This spring 93 maintains a central position of the bung 92 within the hollow which prevents the bung 92 from contacting the screw thread 86. The distal end of the bung is connected to a lever 89. In the current position of the lever 89, the deformable material 91 does not engage the screw thread.

When the lever is actuated the bung 92 is pulled further into the sleeve of deformable material deforming it against its natural bias and into contact with the screw thread 86. In this position any rotation of the mount member 80 with respect to the relatively fixed member 82 causes a vertical displacement of the mount member 80 which is a function of the pitch of the screw thread 86.

When the sleeve of deformable material 91 is not deformed against the screw thread 86, i.e. when the screw thread is disengaged, the three supports 84a, 84b provide a sliding surface along which the mount member 80 may be vertically displaced with respect to the relatively fixed member 82.

The spring 85 which is located substantially at the lengthwise mid-point of the mount member 80 may be replaced or, used in addition to two springs one located at or near each end of the screw thread provided on the mount member 80.

Throughout this specification, the invention has been described using a deformable material to produce a mating thread. The collet which provides the mating thread may, alternatively, be produced from a hard material which has a mating thread formed thereon.

Figure 9:
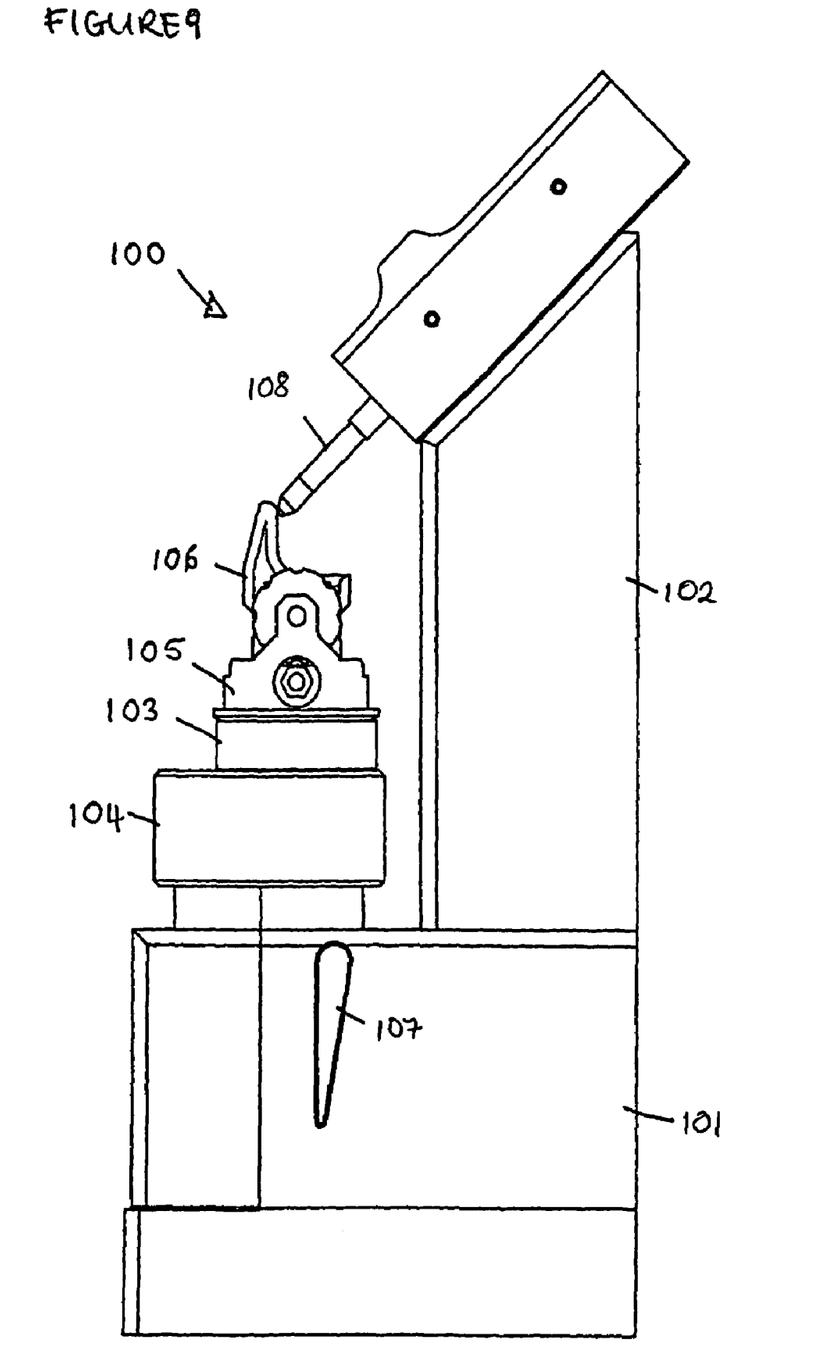
FIG. 9 shows a scanning device according to the invention.

FIG. 9 shows a scanning device 100 having a base portion 101 and a back portion 102. The base portion 101 houses a mount member 103 and a relatively fixed member 104. The mount member 103 has a tooth holder 105 and a tooth 106 mounted thereon. A lever 107 movable between a first and a second position protrudes from the base portion 101 of the scanning device. A probe 108 is attached to the back portion 102 of the scanning device 100.

When the lever 107 is in the first position, the mount member may be simultaneously rotated and moved along a vertical path i.e. describing a spiral or helical path. This first type of movement would allow the surface of the tooth 106 to be scanned by the probe 108. The information gathered by the probe is sent, by any one of a number of ways, to a computer either for translation into the actual surface profile of the tooth or for transmittal to a machine tool which replicates the tooth profile.

When the lever is in the second position, the mount member may be moved along the vertical path independently of any rotation. This second type of movement is useful for setting the start position of a tooth prior to scanning. This is because the speed of rotation of the mount member is determined by the requirements of a scanning device which scans the tooth. The scanning device must maintain good contact with the surface of the tooth being scanned throughout the scanning process. When the surface is non-spherical, The maximum rotational speed for scanning is reduced. In the case of a tooth, 80 rpm is the maximum with 60 rpm being preferred. This means that large scale movement of the mount member in the vertical direction when rotating at around 80 rpm (or faster if the motor used has variable rpm) on a screw thread of pitch 0.2 mm takes up a considerable amount of time that could alternatively be used for scanning another tooth.

For a machining process, the probe could be replaced by a machine tool.

The probe which produces a scan of the surface profile of the sample being scanned may be a contacting probe (as shown in FIG. 9) or a non-contacting probe such as a laser. The probe or machine tool may be at any orientation to the sample holder, for example at 0° or 90° (or anywhere between) to the axis of rotation of the mount member. In some circumstances the use of more than one probe/machine tool may be advantageous.

The probe or machine tool does not have to be fixed in position relative to the mount member but may advantageously be capable of movement vertically and/or in an arcuate path with respect to the rotational axis of the mount member.

After a scanning procedure, the probe could be replaced by a machine tool in order to either produce a replica tooth from a block of ceramic material or to remove unwanted portions of the scanned sample.

A device according to the invention enables helical or spiral movement of a sample by the use of one motor.

Preferably, the screw thread which determines the pitch of the movement is fine and advantageously disengageable from a mating screw thread.

The invention claimed is:

1. A device for the axial and rotational movement of a sample, comprising a mount member for mounting the sample, the mount member being rotatable about an axis and movable along said axis, characterized in that the mount member has a generally helical screw thread which produces the movement along said axis simultaneously with the rotation, wherein the screw thread is disengageable to allow movement of the mount member along the axis without rotation when desired, wherein the screw thread on the mount member co-operates with a screw thread on a relatively fixed member, and the screw threads are relatively movable into and out of engagement with each other, and wherein the screw thread on one of the members is formed from one or more pieces or a layer of a deformable material, which deforms to form a mating screw thread upon being brought into engagement with the screw thread on the other member.

2. A device according to claim 1 wherein the relative movement is actuated by a lever.

3. A device according to claim 1 further comprising a plurality of pieces of a hard material radially spaced around the relatively fixed member.

4. A device according to claim 1 further comprising a probe or machine tool wherein a sample is scanned or machined whilst being axially and rotationally moved.

5. A device according to claim 4 wherein the probe or machine tool is capable of being positioned relative to the rotational axis of the mount member.

6. A device according to claim 4 wherein the sample is a dental part.

7. A device for the axial and rotational movement of a sample, comprising a mount member for mounting the sample, the mount member being rotatable about an axis and movable along said axis, characterized in that the mount member has a generally helical screw thread which produces the movement along said axis simultaneously with the rotation, wherein the screw thread is disengageable to allow movement of the mount member along the axis without rotation when desired, wherein the screw thread on the mount member co-operates with a screw thread on a relatively fixed member, and the screw threads are relatively movable into and out of engagement with each other, and wherein the relative movement is actuated by a lever.

8. A device according to claim 7 further comprising a plurality of pieces of a hard material radially spaced around the relatively fixed member.

9. A device according to claim 7 further comprising a probe or machine tool wherein a sample is scanned or machined whilst being axially and rotationally moved.

10. A device according to claim 9 wherein the probe or machine tool is capable of being positioned relative to the rotational axis of the mount member.

11. A device according to claim 9 wherein the sample is a dental part.

12. A device for the axial and rotational movement of a sample, comprising a mount member for mounting the sample, the mount member being rotatable about an axis and movable along said axis, characterized in that the mount member has a generally helical screw thread which produces the movement along said axis simultaneously with the rotation, wherein the screw thread is disengageable to allow movement of the mount member along the axis without rotation when desired, wherein the screw thread on the mount member co-operates with a screw thread on a relatively fixed member, and the screw threads are relatively movable into and out of engagement with each other, wherein both the screw threads of the mount member and relatively fixed member are permanently formed, and wherein the relative movement is actuated by a lever.

* * * * *